United States Patent [19]

Suda et al.

[11] Patent Number: 5,467,768
[45] Date of Patent: Nov. 21, 1995

[54] MULTI-PURPOSE SENSOR

[75] Inventors: Shin Suda; Hidehiro Hosaka, both of Tokyo, Japan

[73] Assignee: Nihon Koden Corporation, Tokyo, Japan

[21] Appl. No.: 214,127

[22] Filed: Mar. 17, 1994

[30] Foreign Application Priority Data

Mar. 17, 1993 [JP] Japan .................. 5-011773 U

[51] Int. Cl.6 ...................... A61B 5/0205
[52] U.S. Cl. .............. 128/640; 128/671; 128/721
[58] Field of Search ............... 128/716, 721, 128/723, 639–640, 672, 748, 774–782; 607/149–152

[56] References Cited

U.S. PATENT DOCUMENTS

| | | | |
|---|---|---|---|
| 4,516,581 | 5/1985 | Sessions | 128/639 |
| 4,660,562 | 4/1987 | House, Sr. | 128/640 |
| 4,715,235 | 12/1987 | Fukui et al. | 128/716 |
| 4,748,983 | 6/1988 | Shigeta et al. | 128/639 |
| 5,085,217 | 2/1992 | Shimizu | 128/640 |
| 5,195,529 | 3/1993 | Malkamäki | 128/716 |

*Primary Examiner*—Angela D. Sykes
*Assistant Examiner*—Eric F. Winakur
*Attorney, Agent, or Firm*—Sughrue, Mion, Zinn, Macpeak & Seas

[57] ABSTRACT

A multi-purpose sensor a single unit is capable of measuring both electric signals from the object and pressures at the same time and which yet is compact, lightweight and cheap enough to be used as a disposable product. Element in a disk form that is composed of carbon fibers superposed in layers at low density to produce a felt-like texture is surrounded with concentric cylindrical holder. Terminal is connected to an end face of each of element and holder whereas terminal is connected to the other end face, whereby the deformation of element due to an externally applied force is picked up as a voltage change.

7 Claims, 5 Drawing Sheets

MULTI-PURPOSE SENSOR

BACKGROUND OF THE INVENTION

1. Field of the Invention

The present invention relates to a multi-purpose sensor that is to be attached to the skin surface of the object for measuring more than one kind of vital sign.

2. Related Art

Various methods are conventionally used to measure pulse waves in the object or to monitor breathing. If one wants to analyze pressure waves obtained from the body surface non-invasively, they must be measured simultaneously with the recording of an electrocardiogram (hereinafter ECG if applicable). In this case, ECG electrodes are attached to the object but, at the same time, in order to record pulse waves, a pressure transducer such as a piezoelectric element or gage for converting pressure changes to electric signals must be placed over the arterial vessel of interest. In most cases, the pressure transducer is placed over either the right or left common carotid artery or radial artery. If pulse waves are to be detected on the common carotid artery, it is necessary to use a special apparatus for compressing the pressure transducer against the artery from the outside.

Respiratory movements provide important information in monitoring the functions of the patient's body in ICU and other care facilities and they can be measured by various methods including: impedance measurement with two-electrode or four-electrode systems; a belt-type respiratory pickup that detects changes in the resistance of an electrolyte in a tube that expands or contracts in response to thoracic movements; and a thermistor-type respiratory pickup that is attached to the nose for detecting temperature changes due to air flow during breathing.

The above-described methods have their own problems. First, in order to measure pulse waves with the pressure transducer placed over the common carotid artery, the subject must lie quietly on a bed or other supports. In the case of detecting pulse waves on the radial artery, a pressure transducer typically using a piezoelectric element must be attached to the wrist of the subject by winding a belt so that a certain pressure will be exerted on the site of measurement. As a further problem, the use of pressure transducers requires the finding of an appropriate site for attachment, which can only be done by a skilled technician. If the subject moves the wrist to which the sensor is attached, it may be displaced in position to be no longer capable of detecting pulse waves. Hence, this method also requires rest for the subject during measurement and it is extremely difficult to carry out the intended measurement while the subject is carrying on daily activities. What is more, the transducers under consideration are too bulky and expensive to be used as disposable products.

When using the impedance-measuring pickup to monitor respiratory movements, two or four electrodes are attached to the body surface and the changes in resistance that occur in the body tissues between electrodes in response to thoracic movements are detected as changes in respiratory movements. A problem with this approach is that in order to insure that small changes that occur between electrodes are detected as impedance changes, the spacing of two electrodes must be increased.

When using the belt-type pickup, a belt fitted with a tubular sensor is wound around the subject's chest and this gives the subject a feeling of constraint in that part of his body that is tightened by the belt. This is the primary reason why the belt-type pickup is not used very often today. Moreover, the clamping force of the belt must be within reasonable limits, but as a result, the belt is prone to displacement on account of body movements; therefore, measurement with the belt-type pickup also requires the subject to be at rest. It should also be noted that the pickup is too expensive to be used as a disposable product.

The major problem with the use of the thermistor-type pickup which is attached to the nose is the discomfort it causes to the subject. Further, the pickup consumes so much electric power that it is not suitable for use with battery-driven wireless telemeters.

As a further problem, if one wants to record an ECG simultaneously with the measurement of pulse waves or respiration rates, at least two ECG electrodes must be attached to the subject's body in addition to the transducer for measurement of pulse waves or respiration rates. This only adds to the constraint on the side of the subject, who feels greater discomfort or pain.

SUMMARY OF THE INVENTION

The present invention has been accomplished under these circumstances and has as an object providing a multi-purpose sensor including a single unit which is capable of simultaneously measuring electric signals from the object and pressure and which is compact, lightweight and cheap enough to be used as a disposable product.

An object of the present invention is to provide a multi-purpose sensor to be attached to the skin surface of a subject for detecting more than one kind of vital sign from the subject. The multi-purpose sensor comprise an element formed as a disk of conductive fibers, a holder that surrounds the outer circumference of said element, with an adhesive layer provided on one end face, and which is generally the same in thickness as said element, and a pair of terminals that are held on both end faces of said holder and which are connected electrically to both end faces of said element.

According to the multi-purpose sensor of the present invention, one of the terminals that is on the side for contacting the skin surface of the subject is formed in a shape that covers the entire part of an end face of the element, whereas the face of that one terminal which is to contact the skin surface is covered with an insulation layer, with a conductive solid gel being packed between the outer circumference of the element and the inner circumference of the holder. The conductive solid gel may be prepared from super-absorbent polymers such as carboxymethyl cellulose, acrylic acid and polyvinyl alcohol.

According to the multi-purpose sensor of the present invention, the element and the holder are each provided with a conductive solid gel layer on the end face which is to contact the skin surface of the subject.

According to the multi-purpose sensor of the present invention, the element and the holder are provided on one end face with a conductive solid gel layer and a second holder having a paste reservoir, respectively.

According to the multi-purpose sensor of the present invention, the terminal on the side closer to the skin is formed in two layers, with an insulation layer being interposed.

The element in the multi-purpose sensor of the present invention is composed of conductive fibers that are produced in a felt-like texture, in which they are intertwined in such an intricate manner that they will contact each other at a greater number of points when an external force is applied. If the sensor is preliminarily supplied with a specified current, the increase in the number of fiber contact points will lead to a lower dc resistance, which is observed as a change in the voltage across the sensor. By measuring this voltage change, the analyst can recognize the change in the externally applied force, thereby detecting pulse waves or respiratory variations. If desired, one of the two terminals that is on the side for contacting the skin surface of the subject may be used as a terminal electrode for detecting biological electric signals as in the recording of ECG.

In the multi-purpose sensor of the present invention, the end face of the element that will contact the skin surface is provided with a conductive solid gel or a paste reservoir which, in turn, are provided with a second holder on the outer circumference. This arrangement offers the advantage that the adhesive layer provided on the end face of the second holder that is to contact the skin surface acts together with the conductive solid gel or paste to thereby fix the sensor securely to the skin surface.

In the multi-purpose sensor of the present invention, the terminal on the side in contact with the skin surface is formed in two layers, with an insulation layer being interposed. Hence, the terminal on the side closer to the skin surface can be used for detecting biological electric signal, as in the recording of ECG, whereas both the inner terminal and the terminal connected to the end face remote from the element can be used for detecting the change in the externally applied force. Thus, biological electric signals can be detected in a very consistent manner by means of the separate terminal which can be used independently of other terminals.

BRIEF DESCRIPTION OF THE DRAWINGS

FIG. 5 (b) is a diagram showing a respiratory waveform obtained by the measurements with the circuit shown in FIG. 4;

DETAILED DESCRIPTION OF THE PREFERRED EMBODIMENTS

Examples of the multi-purpose sensor of the present invention are described below with reference to the accompanying drawings.

Figure 1:
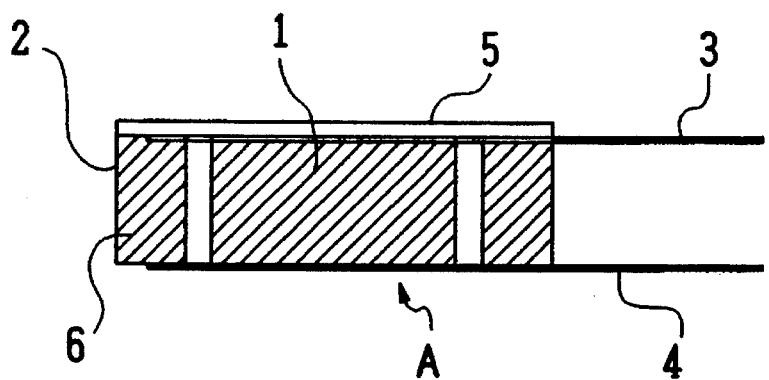
FIG. 1 is a cross section of a multi-purpose sensor according to the first example of the present invention.
Figure 2:
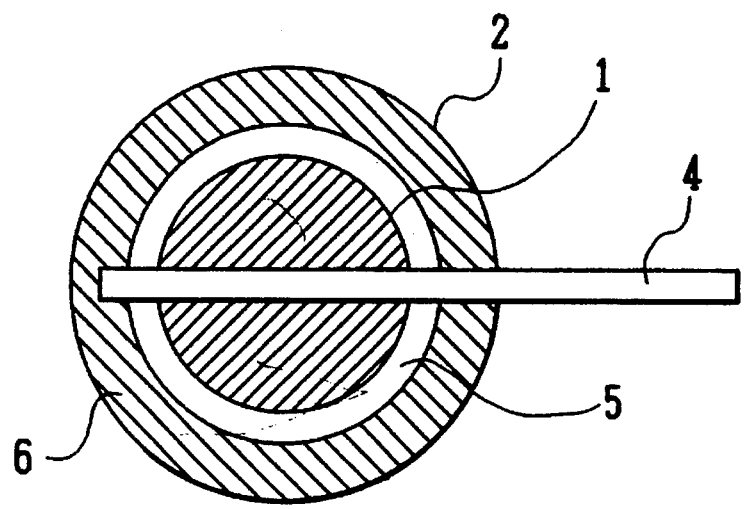
FIG. 2 is a bottom view of the sensor of FIG. 1 as seen in the direction of arrow A.
Figure 3:
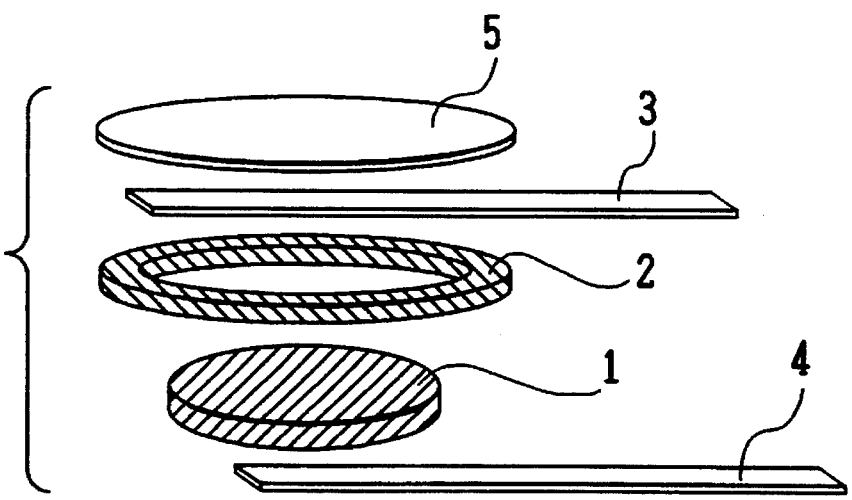
FIG. 3 is an exploded view of the sensor of FIG. 1.

FIGS. 1 to 3 show construction of a multi-purpose sensor according to the first example of the present invention. As shown in these figures, an element 1 in a cylindrical form is composed of carbon fibers that are produced in a felt-like texture. The element 1 is surrounded by a concentric cylindrical holder 2 that is formed of a foam tape or the like and which is spaced from the outer circumference of the element 1. Of course, the shape of the element 1 and the holder 2 are not limited by this embodiment. The element 1 and the holder 2 have substantially the same height in the axial direction. A terminal 3 is connected diametrically to an end face of each of the element 1 and the holder 2, and a terminal 4 is connected diametrically to the other end face of each member. The end face of each of the element 1 and the holder 2 to which the terminal 3 is connected is covered with a label 5 in such a way that it also covers the terminal 3. The other end face of the holder 2 is provided with an adhesive layer 6.

Let us describe the mechanism of the action in the first example. Element 1 is a felt-like material in which conductive carbon fibers are intertwined in a coarsely but intricate pattern and, hence, the fibers will contact each other at a greater number of points when an external force is exerted. If the element is preliminarily supplied with a specified current via terminals 3 and 4, the increase in the number of fiber contact points will lead to a smaller dc resistance in the element 1, which can be observed as a change in the voltage between terminals 3 and 4. Assume here that the element 1 has a thickness of 5 mm and a diameter of 10 mm and that it has a dc resistance of 100 Ω in the absence of applied external force. If the thickness of this element decreases by 0.5 mm upon application of an external force, its dc resistance will drop to 80 Ω. The resistance of carbon fibers varies with the calcination temperature but, generally speaking, those carbon fibers which have higher resistances are easier to use in the element 1 of the multi-purpose sensor according to the example under consideration. Conductive rubber is another example of materials that will experience a change in dc resistance if they are formed under an applied pressure. However, conductive rubber is not suitable for use in the detection of pulse waves or respiratory vibrations since a very great external force must be applied in order to cause the measurable change in voltage between terminals 3 and 4.

Figure 4:
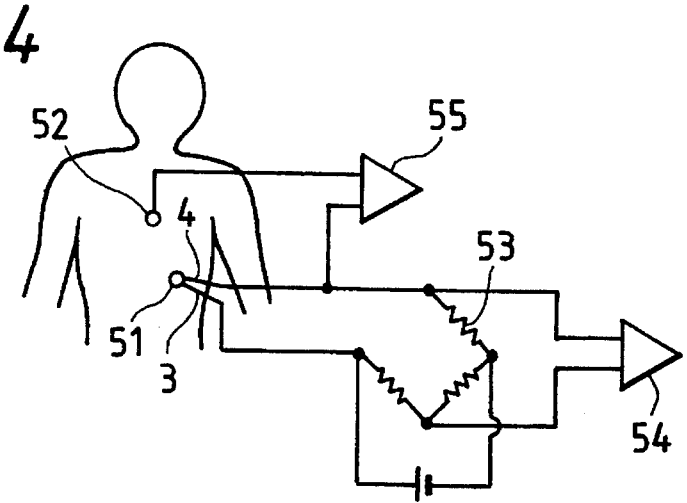
FIG. 4 is a wiring diagram for signal detection with the sensor of FIG. 1.

For detecting pulse waves with the multi-purpose sensor having the element 1, the sensor is attached to the wrist, the neck or some other site where an artery runs, with the adhesive layer 6 on the holder 2 being interposed, and pulse waves are detected as voltage changes that can be read with the element 1. For detecting respiratory variations, the sensor is attached to the subject's chest as shown in FIG. 4, where the sensor is indicated by 51. For detecting biological electric signals as in the recording of ECG, a common biological electrode 52 and sensor 51 are attached to specified sites on the skin surface and the intended detection is performed through terminal 4.

Figure 5A:
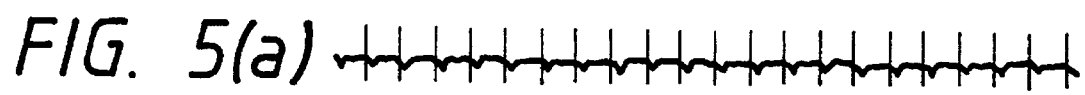
FIG. 5 (a) is a diagram showing an ECG obtained by the measurements with the circuit shown in FIG. 4.
Figure 5B:

FIG. 4 is a wiring diagram for the case where both respiratory variations and ECG are detected using the multi-purpose sensor 51 and biological electrode 52. Terminals 3 and 4 on the multi-purpose sensor 51 are connected to an amplifier 54 via a bridge circuit 53 and breathing waveforms are detected by the output of amplifier 54. Terminal 4 on the multi-purpose sensor 51 and ECG electrode 52 are connected to another amplifier 55, the output of which will detect ECG. FIG. 5 (a) and (b) show recordings obtained by the measurements.

According to the first example just described above, biological electric signals and pressure signals can be detected simultaneously with a single unit of the element 1 and, hence, the sensor can be manufactured in small size and light weight and at a low enough price to be usable as a disposable product.

Figure 6:
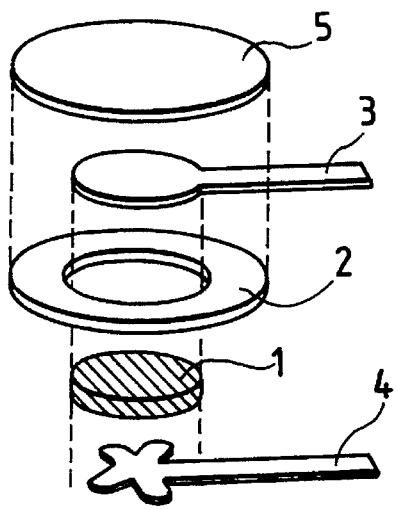
FIG. 6 is an exploded view of a sensor according to a modification of the first example.

The shape of that part of terminals 3 and 4 which is to be connected to the element 1 is in no way limited to the case shown in FIG. 1 and the shape may be as shown in FIG. 6, in which terminal 3 has a circular portion that is substantially equal in diameter to the element 1 and in which terminal 4 has a cross in the element connecting portion so that part of the element 1 can make direct contact with the skin.

Other examples of the multi-purpose sensor of the present invention are shown in FIGS. 7 to 13, in which those parts which have counterparts in the example shown in FIGS. 1 to 3 are identified by like numerals and will not be described in detail.

Figure 7:
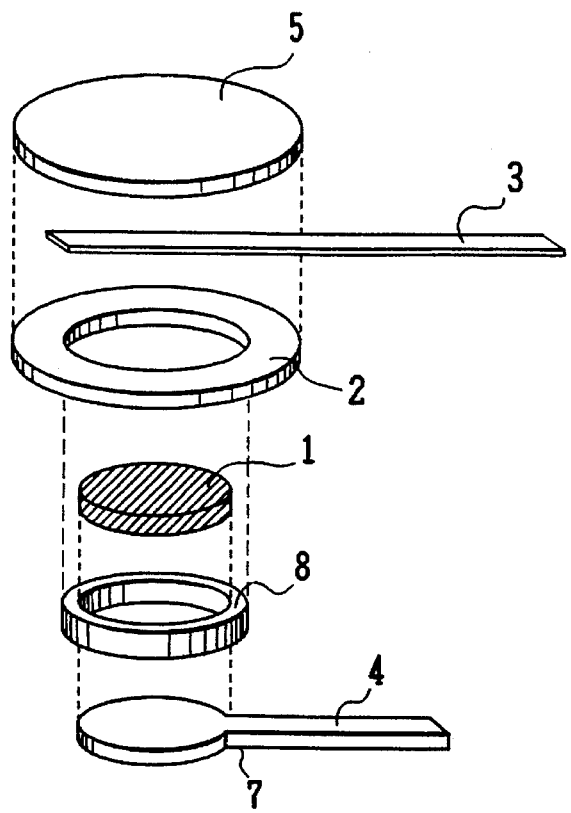
FIG. 7 is an exploded view of a multi-purpose sensor according to the second example of the present invention.

FIG. 7 shows the second example of the present invention. If sweat and other moisture contents that originate from the skin during measurement permeate into the element 1, the latter will become electrically conductive in the entire part to eventually make pressure detection impossible. The second example is designed to avoid this problem; that part of the terminal 4 which is to be connected to an end face of the element 1 is so shaped that it will cover that end face entirely and the face of that part which is to contact the skin surface is covered with an insulation layer 7 and, in addition, a conductive gel 8 is packed between the inner periphery of the holder 2 and the outer periphery of the element 1. Biological electric signals will be transmitted from the skin surface through the conductive gel 8 to reach the side of terminal 4 where no insulation is provided.

Figure 8:
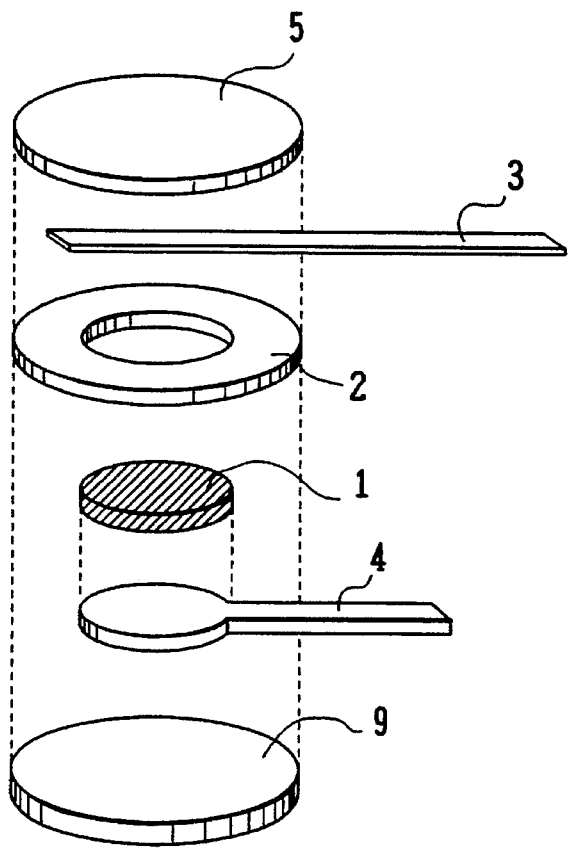
FIG. 8 is an exploded view of a multi-purpose sensor according to the third example of the present invention.

FIG. 8 shows the third example of the present invention, in which the element 1 and the holder 2 are provided with a conductive solid gel layer 9 on the end face that is closer to the skin surface.

The second and third examples will achieve the same advantages as the aforementioned first example.

Figure 9:
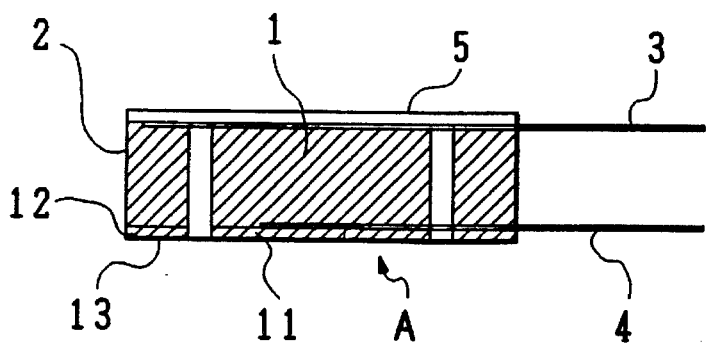
FIG. 9 is a cross section of a multi-purpose sensor according to the fourth example of the present invention.
Figure 10:
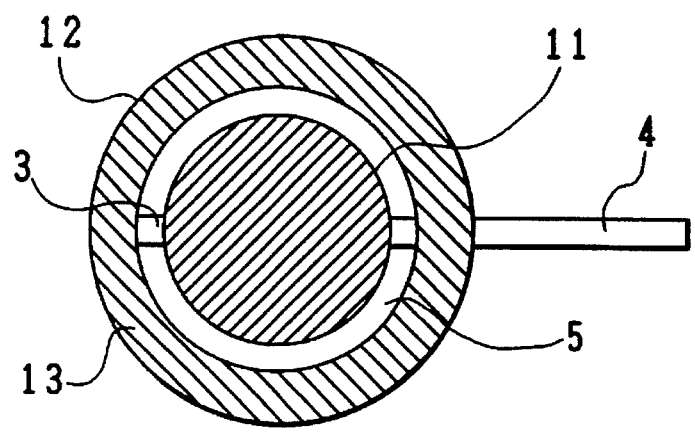
FIG. 10 is a bottom view of the sensor of FIG. 9 as seen in the direction of arrow A.
Figure 11:
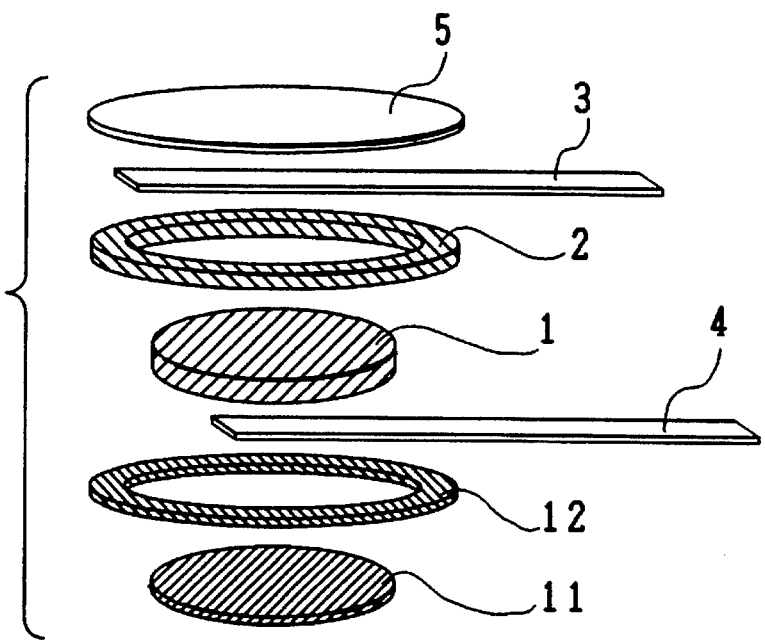
FIG. 11 is an exploded view of the sensor of FIG. 9.

FIGS. 9 to 11 show the fourth example of the present invention. The end face of the element 1 that is remote from the side where the label 5 is attached is provided with a conductive solid gel layer 11 that is large enough to cover not only the element 1 but also part of the terminal 4. In addition, a second annular holder 12 is bonded to the end face of the first holder 2 that is on the same side as where the conductive solid gel layer 11 is provided and the second holder 12 in turn is provided with an adhesive layer 13 at the end face on the outer side. It should be noted that one end of the terminal 4 to the sensor of the fourth example does not project beyond the outer periphery of the element 1.

When the multi-purpose sensor of the fourth example is to be attached to the skin surface, element 1 contacts the skin surface via the conductive solid gel layer 11 and the second holder 12 via the adhesive layer 13 and this insures the sensor to be fixed securely to the skin surface.

Figure 12:
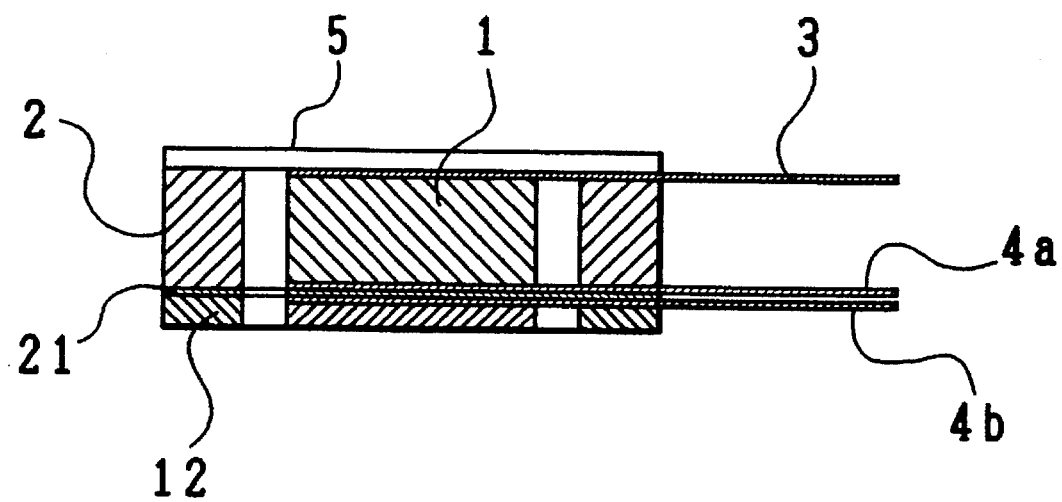
FIG. 12 is a cross section of a multi-purpose sensor according to a modification of the fifth example.
Figure 13:
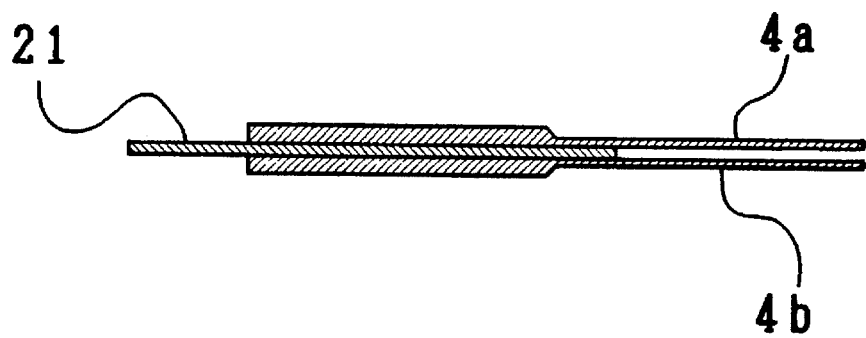
FIG. 13 is a partial enlarged cross section of FIG. 12.

FIGS. 12 and 13 show the fifth example of the present invention which is a modification of the fourth example. In this example, terminal 4 of the same type as shown in FIGS. 9 to 11 is composed of two layers 4a and 4b. Layer 4a which is connected to the element 1 is coated or plated with carbon on the surface, whereas layer 4b which is connected to the conductive solid gel layer 11 is coated or plated with Ag or AgCl on the surface. Layers 4a and 4b are spaced apart by a film 21 that works as an insulation layer and which extends to the entire outer circumference of the holders 2 and 12.

Because of the presence of the intervening film 21, the conductive solid gel 11 need not be a solid gel in the strict sense of the term and may be replaced by common water-base paste that has NaCl or KCl incorporated as an electrolyte in order to prevent the entrance of moisture into the element 1. In that case, the center hole in the second holder 12 will function as a paste reservoir.

In the fifth example, changes in an externally applied force are detected at terminals 3 and 4a whereas vital signals to be recorded as on ECG can be detected at terminal 4b. Thus, vital signals can be detected consistently with terminal 4b which functions independently of other terminals 3 and 4a.

The foregoing description of the examples of the present invention assumes the case where the element 1 is composed of carbon fibers but this is not the sole case of the invention and the element 1 may be composed of other conductive fibers such as stainless steel fibers.

It should also be mentioned that in the examples described above, one end of the terminal 3 may be so shaped as to cover the entire surface of the holder 2 and if this is done, label 5 may be omitted.

As described on the foregoing pages, the multi-purpose sensor of the present invention has a terminal connected to each end face of a element that is composed of conductive fibers; hence, a single unit of the sensor can detect biological pressure changes such as pulse wave variations and the respiration status while, at the same time, it can detect biological electric signals as in the recording of ECG. As a further advantage, the sensor can be manufactured as a compact, lightweight, inexpensive and, hence, disposable product.

What is claimed is:

1. A multi-purpose sensor for detecting more than one kind of vital sign from a subject, when the sensor is attached to the skin surface of the subject, the multi-purpose sensor comprising:

an element formed of conductive fibers in a shape of a plate having a top face and a bottom face, said bottom face being closer than said top face to the skin surface of the subject;

a flat holder having a top face and a bottom face and a center hole, said flat holder disposed around an outer perimeter of said element, an adhesive layer being provided on said bottom face of said holder, said holder being no more than generally the same in thickness as said element; and a pair of terminals respectively connected electrically to both said top and said bottom faces of said element and held on both said top and said bottom faces of said holder, a first of said terminals being connected to said top faces and a second of said terminals being connected to said bottom faces.

2. A multi-purpose sensor as claimed in claim 1, further comprising:

a conductive solid gel packed between said outer perimeter of said element and said center hole of said flat holder,
 wherein said second of said terminals is formed in a shape in such a manner that said second of said terminals completely covers said bottom face of said element and said second terminal has a face which is to contact the skin surface, said second terminal face being covered with an insulation layer.

3. A multi-purpose sensor as claimed in claim 1, further comprising:

a conductive solid gel layer provided on said bottom face of said element.

4. A multi-purpose sensor as claimed in claim 1, further comprising:

an auxiliary holder having a center hole, said auxiliary holder provided facing said bottom face of said flat holder, said auxiliary holder disposed around said outer perimeter of said element; and a conductive solid gel layer provided on said bottom face of said element.

5. A multi-purpose sensor as claimed in claim 1, further comprising:

a flat auxiliary holder having a center hole, provided facing said bottom face of said flat holder, said auxiliary holder disposed around said outer perimeter of said element, said auxiliary holder being slightly less in thickness than said element, wherein said second terminal includes:

a pair of terminal layers;

an insulating layer interposed between said terminal layers; and a paste accommodated in said center hole of said auxiliary holder.

6. A multi-purpose sensor as claimed in claim 1, wherein said first terminal is shaped to completely cover said top face of said holder.

7. A multi-purpose sensor as claimed in claim 1, further comprising:

a cover for completely covering said bottom face of said holder.

* * * * *